United States Patent
Solf et al.

(10) Patent No.: US 9,445,774 B2
(45) Date of Patent: Sep. 20, 2016

(54) ENERGY APPLICATION APPARATUS

(75) Inventors: Torsten Solf, Aachen (DE); Carolina Ribbing, Aachen (DE); Petrus Wilhelmus Helena Van Loon, Asten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 222 days.

(21) Appl. No.: 14/113,387

(22) PCT Filed: Apr. 25, 2012

(86) PCT No.: PCT/IB2012/052063
§ 371 (c)(1),
(2), (4) Date: Oct. 23, 2013

(87) PCT Pub. No.: WO2012/147034
PCT Pub. Date: Nov. 1, 2012

(65) Prior Publication Data
US 2014/0051904 A1    Feb. 20, 2014

(30) Foreign Application Priority Data
Apr. 27, 2011   (EP) .................................. 11305497

(51) Int. Cl.
*G01T 1/24*      (2006.01)
*A61B 6/00*      (2006.01)
(Continued)

(52) U.S. Cl.
CPC ........... *A61B 6/4258* (2013.01); *A61N 5/1001* (2013.01); *G01V 5/0041* (2013.01); *A61B 6/037* (2013.01); *A61N 2005/1052* (2013.01); *A61N 2005/1061* (2013.01)

(58) Field of Classification Search
CPC ............. G01V 5/0041; G01V 5/0025; G01V 5/0016; A61B 6/48; A61N 5/1001

USPC .......................................... 250/370.08; 600/3
See application file for complete search history.

(56) References Cited

U.S. PATENT DOCUMENTS 5,694,933 A * 12/1997 Madden ............... A61B 6/4057
250/363.02
6,193,763 B1    2/2001 Mackin
(Continued)

FOREIGN PATENT DOCUMENTS

JP       2004512502       4/2004
WO        0045855 A2      8/2000
(Continued)

OTHER PUBLICATIONS

Watabe, H., et al.; Development of a Miniature Gamma-Ray Endoscopic Probe for Tumor Localization in Nuclear Medicine; 1993; IEEE Trans. on Nuclear Science; 40(2)88-94.

*Primary Examiner* — David Porta
*Assistant Examiner* — Abra Fein (57) ABSTRACT

An energy application apparatus applies energy to an object. The object (2), such as a tumor which has absorbed a radioisotope tracer, defines a location (3) of radioactive material. A location detection unit detects the location with the radioactive material. An x-ray unit applies x-rays to the detected location of the object. Since the location, to which energy should be applied, includes radioactive material, this location can be accurately detected by using the location detection unit. Moreover, since the application of the x-rays can be well controlled by controlling, for example, the intensity and the energy spectrum of the x-rays, energy can be accurately applied to the accurately detected location. The overall process of applying energy to the object can therefore be performed with increased accuracy.

21 Claims, 5 Drawing Sheets

(51) Int. Cl.
*G01V 5/00* (2006.01)
*A61N 5/10* (2006.01)
*A61B 6/03* (2006.01)

(56) References Cited

U.S. PATENT DOCUMENTS

| | | | |
|---|---|---|---|
| 6,241,670 B1 | 6/2001 | Nambu | |
| 6,295,680 B1 | 10/2001 | Wahl et al. | |
| 6,362,472 B1* | 3/2002 | Yarnall | G01T 1/161 |
| | | | 250/252.1 |
| 6,512,943 B1* | 1/2003 | Kelcz | A61B 17/3403 |
| | | | 600/431 |
| 6,856,670 B2 | 2/2005 | Hoheisel | |
| 7,373,197 B2 | 5/2008 | Daighighian et al. | |
| 7,662,083 B2 | 2/2010 | Gueye et al. | |
| 2004/0015075 A1 | 1/2004 | Kimchy et al. | |
| 2004/0016886 A1 | 1/2004 | Ringermacher et al. | |
| 2004/0165699 A1 | 8/2004 | Rusch et al. | |
| 2004/0218720 A1* | 11/2004 | Swanson | A61N 5/1001 |
| | | | 378/119 |
| 2006/0113482 A1 | 6/2006 | Pelizzari et al. | |
| 2006/0163495 A1* | 7/2006 | Hiramoto | A61N 5/1049 |
| | | | 250/492.3 |
| 2006/0173232 A1 | 8/2006 | Lovoi et al. | |
| 2006/0173233 A1 | 8/2006 | Lovoi | |
| 2008/0200803 A1 | 8/2008 | Kwon et al. | |
| 2008/0237482 A1* | 10/2008 | Shahar | A61B 6/06 |
| | | | 250/394 |
| 2009/0309046 A1* | 12/2009 | Balakin | A61N 5/1049 |
| | | | 250/492.3 |
| 2010/0010343 A1 | 1/2010 | Daghighian et al. | |
| 2010/0179522 A1 | 7/2010 | Companion et al. | |

FOREIGN PATENT DOCUMENTS

| | | |
|---|---|---|
| WO | 0164286 A1 | 9/2001 |
| WO | 2007067445 A2 | 6/2007 |
| WO | 2009109879 A2 | 9/2009 |
| WO | 2009114117 A2 | 9/2009 |

* cited by examiner

ENERGY APPLICATION APPARATUS

FIELD OF THE INVENTION

The invention relates to an energy application apparatus, an energy application method and an energy application computer program for applying energy to an object. The invention relates further to an interventional device being at least one of a handheld device and an in-body device for applying energy to an object and to a control device for controlling the interventional device.

BACKGROUND OF THE INVENTION

US 2008/0200803 A1 discloses a cancer detection and treatment instrument comprising a first conductive plate and a second conductive plate which is opposed to the first conductive plate and has a first opening. A first signal line is disposed between the first conductive plate and the second conductive plate, and one end of a first contact member is exposed through the first opening and another end of the first contact member is connected to the first signal line. A dielectric portion is filled between the first and second conductive plates and the first signal line, and a conductive layer surrounds both side surfaces and a front end surface of the dielectric portion, wherein the surfaces are exposed. The cancer detection and treatment instrument further comprises a monolithic microwave integrated circuit supplying a detection-specific ultrahigh-frequency signal and a detection-specific ultrahigh-frequency power to the first signal line and receiving reflected signals through the first signal line. A digital signal processor receives the reflected signals from the monolithic microwave integrated circuit, analyzes electromagnetic characteristics of the reflected signals, and controls a treatment-specific ultrahigh-frequency power in accordance with the analysis result. The microwave-base detection and treatment of cancer regions may have a reduced accuracy only. For example, also larger parts of healthy tissue may be detected and treated as cancer region.

SUMMARY OF THE INVENTION

It is an object of the present invention to provide an energy application apparatus for applying energy to an object, wherein a location, to which energy should be applied, and the application of energy to this location can be performed with increased accuracy.

In a first aspect of the present invention an energy application apparatus for applying energy to an object is presented, wherein the object comprises a location with radioactive material and wherein the energy application apparatus comprises:

a location detection unit being usable for detecting the location with the radioactive material, and an x-ray unit for applying x-rays to the detected location of the object.

Since the location, to which energy should be applied, comprises radioactive material, this location can be accurately detected by using the location detection unit. Moreover, since the application of the x-rays can be well controlled by controlling, for example, the intensity and the energy spectrum of the x-rays, energy can be accurately applied to the accurately detected location. The overall process of applying energy to the object can therefore be performed with increased accuracy.

The object is, for example, a person having lymph nodes, which may have accumulated the radioactive material being a tracer, for example, a gamma emitter like Tc-99 with an energy of 140 keV and six hours half-life. The tracer may be enriched in lymph nodes which contain cancer cells. Metastased lymph nodes may therefore be detected and treated by applying the x-rays to the detected lymph nodes.

The radioactive material can also be a radioactive glucose component like fluorodeoxyglucose (FDG), wherein the F-18 of FDG decays through positron emission with a half-life of 110 min. The emitted positrons annihilate with electrons producing 511 keV photons. FDG can be used for detecting bowel and liver tumors. It can be used for diagnosis, staging and treatment monitoring also of many other cancer forms like colorectal, lung, melanoma, breast, Hodgin's disease, and non-Hodgin's lymphoma. The radioactive material can be provided by injecting the same in a dose of, for example, 5 to 10 mCi, which corresponds to 185 to 370 MBq.

It is preferred that the energy application apparatus comprises an interventional device being at least one of a handheld device and an in-body device, wherein the interventional device includes at least a part of the location detection unit and at least a part of the x-ray unit such that the location with the radioactive material is detectable and x-rays are applicable to the detected location via the interventional device. The handheld device, which may also be regarded as being a handheld probe, can have a pen-like shape and the in-body device can be a catheter or a needle. The handheld device is preferentially usable in open, but minimally invasive surgery, wherein a user can detect the location with the radioactive material and apply the x-rays to the detected location by using the handheld device. If the interventional device is a catheter or a needle, the catheter or needle can be introduced into the person to be treated for detecting the location with radioactive material and for applying x-rays to the detected location. Detection elements of the location detection unit and an x-ray emitting part of the x-ray unit are preferentially located at a tip of the interventional device.

It is further preferred that the location detection unit comprises an array of detection elements for detecting radiation from the radioactive material and for generating a detection signal being indicative of the detected radiation. The array of detection elements is preferentially a scintillation detector array or a direct conversion material detector array. For example, the array of detection elements can be a SiPM or digital SiPM based scintillation detector array or a CZT based direct conversion material detector array. The detection signal can be indicative of the energy, the arrival time and/or the position of the respective incoming event, i.e. the detected radiation.

The array of detection elements can be located in two or more regions embracing at least a part of the x-ray unit. Moreover, the array of detector elements can be located on a cylindrical holder covered on its outside with the array of detector elements, wherein at least a part of the x-ray unit is located within the holder. The x-ray unit is preferentially slidable out off the holder at a distal end of an interventional device of the energy application apparatus for allowing the x-ray unit to apply x-rays to the object.

The array of detection elements is preferentially adapted to generate a spatial detection signal depending on the location of the respective detection element, wherein the energy application apparatus comprises a direction determination unit for determining a direction of maximal radioactivity based on the spatial detection signal. It is further preferred that the direction determination unit is adapted to differentiate the spatial detection signal and to determine the direction of maximal radioactivity based on the differentiated spatial detection signal. Moreover, the energy application apparatus comprises preferentially an output unit for outputting the detected direction of maximal radioactivity. In particular, the apparatus can comprise a display for displaying the detected direction to a user. The display can be provided on the interventional device, for example, on a handheld device like a handheld probe, and/or the display can be provided externally of the interventional device, in particular, externally of the handheld device. By providing the direction of maximal radioactivity an indication for the direction is given, in which the location with the radioactive material is located. A user can therefore move the energy application apparatus, in particular, the interventional device, in the direction of maximal radioactivity, in order to find the location with the radioactive material, which is to be treated by applying the x-rays to this location.

In a preferred embodiment, the array of detection elements is adapted to allow detecting an energy resolved spectrum of the detected radiation, wherein the energy application apparatus further comprises an activity determination unit for determining an activity of the radioactive material depending on the detected energy resolved spectrum. In particular, the detected spectrum can be compared with a target spectrum and the activity of the radioactive material can be determined depending on the comparison. This allows determining a specific activity being the activity of a specific radioactive material labeling a location of the object, to which the x-rays should be applied, i.e. it can be distinguished between different radioactive materials, if different radioactive materials are present in the object.

Also the determined activity can be shown on the output unit, in particular, on the display.

It is further preferred that the array of detection elements is switchable between a counting mode, in which single detected radioactive events are detected, and an integrating mode, wherein the energy application apparatus further comprises a detection and x-ray application control unit for controlling the location detection unit such that the array of detection elements is operated in the counting mode, when the x-rays are not applied, and that the array of detection elements is operated in the integrating mode, when the x-rays are applied, wherein, when the x-rays are applied, the array of detection elements detects scattered x-rays scattered by the object and wherein the detection and x-ray application control unit is adapted to control the x-ray unit depending on the scattered x-rays. The scattered x-rays provide a feedback, which allows improving the control of the application of the x-rays.

It is also preferred that the energy application apparatus comprises a positioning unit for determining the position of at least a portion of the energy application apparatus with respect to a reference coordinate system. The positioning unit comprises, for example, at least one of a differential GPS sensor, a fibre Bragg grating (FBG) sensor, an electromagnetic (EM) sensor, et cetera. Preferentially, the positioning unit is arranged at an interventional device of the energy application apparatus. The positioning unit provides preferentially a positioning signal to a position calculation unit for calculating the position of at least a portion of the energy application apparatus with respect to a reference coordinate system.

In a preferred embodiment, the energy application apparatus further comprises an image providing unit for providing an image of the object, which is registered with respect to the reference coordinate system, and a display for showing the determined position of at least the portion of the energy application apparatus with respect to the object. The apparatus is preferentially used for an interventional procedure and the provided image was preferentially generated before the interventional procedure. The image is, for example, a positron emission tomography (PET) image, a single photon emission computed tomography (SPECT) image, a computed tomography (CT) image, a magnetic resonance (MR) image or an ultrasound image. The image can also be an image of another imaging modality. The reference coordinate system is, for example, defined by the imaging modality used for generating the image of the object. The position of at least a portion of the energy application apparatus is preferentially determined in real-time, thereby allowing navigating the apparatus based on the determined position, which may be shown with respect to the object on a display.

It is further preferred that the energy application apparatus comprises an x-ray detection element for detecting scattered x-rays scattered from the object and a control device for controlling the application of the x-rays depending on the detected scattered x-rays. Thus, the energy application apparatus can comprise an array of detection elements, which can be used for detecting the location of the radioactive material and for detecting scattered x-rays, as described above, or the energy application apparatus can comprise separate detection elements, an array of detector elements for detecting the location of the radioactive material and an x-ray detection element for detecting scattered x-rays. If separate detectors are used for detecting the location of the radioactive material and for detecting scattered x-rays, the location of the radioactive material can be detected simultaneously with detecting scattered x-rays. Moreover, the different detectors can each be optimized for the respective detection.

In a further aspect of the present invention an interventional device being at least one of a handheld device and an in-body device for applying energy to an object is presented, wherein the interventional device comprises at least a part of a location detection unit, which is usable for detecting a location with radioactive material, and at least a part of an x-ray unit for applying x-rays to the detected location of the object such that the location with the radioactive material is detectable and x-rays are applicable to the detected location via the interventional device.

In a further aspect of the present invention a control device for controlling the interventional device is presented, wherein the control device is adapted to control at least one of a) the location detection unit for controlling the detection of the location with radioactive material and b) the x-ray unit for controlling the application of x-rays to the detected location.

In a further aspect of the present invention an energy application method for applying energy to an object is presented, wherein the object comprises a location with radioactive material and wherein the energy application method comprises:

detecting the location with the radioactive material, and
applying x-rays to the detected location of the object by an x-ray unit.

In a further aspect of the present invention an energy application computer program for applying energy to an object is presented, wherein the computer program comprises program code means for causing an energy application apparatus to carry out the steps of the energy application method, when the computer program is run on a computer controlling the energy application apparatus.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
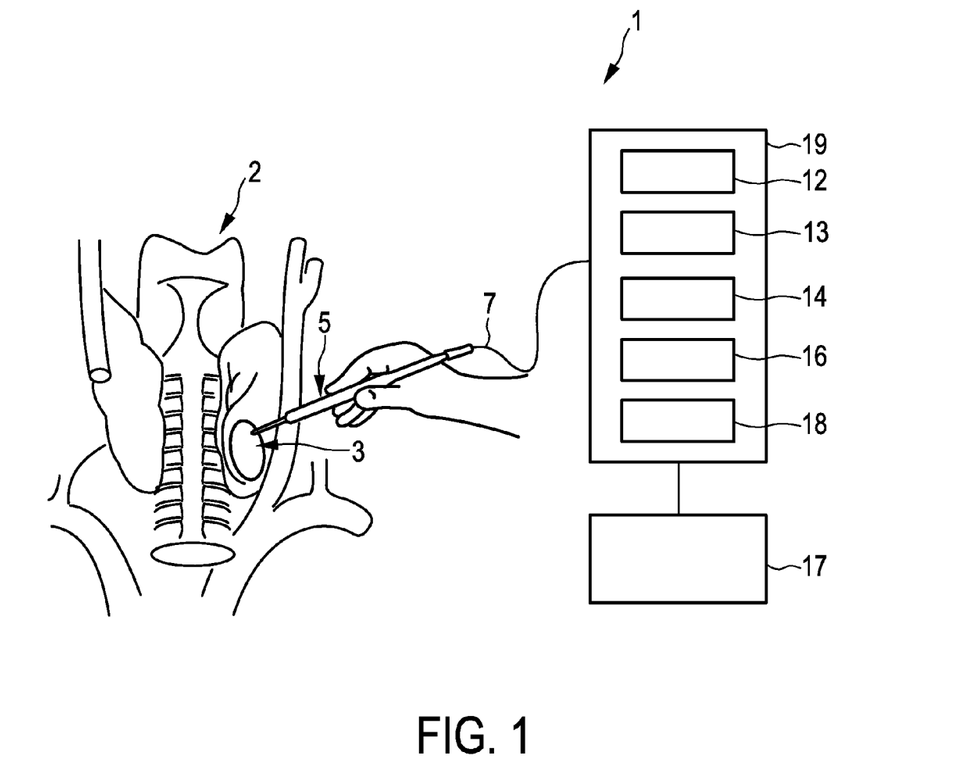
FIG. 1 shows schematically and exemplarily an embodiment of an energy application apparatus for applying energy to an object.

FIG. 1 shows schematically and exemplarily an embodiment of an energy application apparatus 1 for applying energy to an object 2. The object 2 is, in this embodiment, the neck portion of a person. The object 2 comprises a location 3 with radioactive material, wherein the energy application apparatus 1 comprises a location detection unit 8 being usable for detecting the location 3 with radioactive material and an x-ray unit 9 for applying x-rays to the detected location 3 of the object 2.

The energy application apparatus 1 comprises an interventional device 5 being a handheld probe, which includes at least a part of the location detection unit and at least a part of the x-ray unit such that the location 3 with the radioactive material is detectable and x-rays are applicable to the detected location 3 via the handheld probe 5. The handheld probe 5 is connected with a control device 19 via a connection element like a cable 7. The handheld probe 5 has a pen-like shape and can be held by the hand of a user like a pen. The handheld probe 5 is schematically and exemplarily shown in more detail in FIG. 2.

Figure 2:
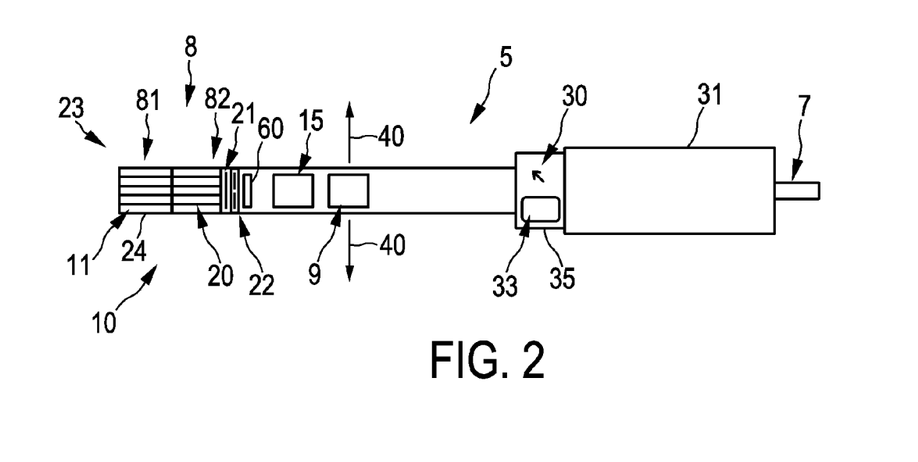
FIG. 2 shows schematically and exemplarily an embodiment of a handheld probe of the energy application apparatus.

The location detection unit 8 of the handheld probe 5 comprises a first radial scintillator array 81 and a second radial scintillator array 82, which are located at different axial positions with respect to the handheld probe 5 at the tip 23. The first and second radial scintillator arrays 81, 82 comprise collimators 11, 20 for collimating the radiation received from the radioactive material before being received by the respective radial scintillator array. The radial scintillator arrays 81, 82 are connected with digital SiPMs 22 via light guides 21, wherein only the light guide between the second radial scintillator array 82 and the digital SiPMs 22 is shown for clarity reasons. The digital SiPMs are an array of single photon detection devices, wherein in other embodiments instead of the digital SiPMs another array of single photon detection devices can be used. For example, also a SiPM based scintillation array detector or an array with a direct conversion material like CZT or CdTe could be used. The array 10 of detection elements can be adapted to generate a detection signal being at least depending on the location of the respective detection element. In particular, the generated detection signal can provide information about the energy in keV, the arrival time in sub-ns and the location of the respective detection element, which has detected a respective incoming event. The accuracy of determining the location of the respective detection element is preferentially 1 mm or smaller. The tip 23 of the handheld probe 5 comprises preferentially a protective cover material 24, which can be sterilized, for enclosing the different elements of the handheld probe 5.

The scintillator arrays 81, 82 comprise a scintillation material like NaI, LY—SO or LaBr. The scintillation material converts incoming radiation into light having a wavelength being detectable by the array of single optical photon detection devices 22 based on digital SiPMs. The scintillation material is chosen to have a large conversion efficiency such that thin layers reduce the absorption of radiation dose by the scintillator layer without compromising the sensitivity of the dose sensor.

In the embodiment shown in FIG. 2, the collimators 11, 20 are adapted to collimate and receive radiation in radial direction, i.e. preferentially the collimators 11, 20 are aligned in radial direction. However, in another embodiment, the array of detection elements can also be adapted to detect radiation in a forward direction, i.e. the array of detection elements can be adapted to receive radiation coming from the left side in FIG. 2. In this case, the collimator can be formed by parallel holes in the outer cover 24 of the handheld probe 5. In another embodiment, a collimator can be provided in another way. For example, multiple pinholes can be provided in the outer cover of the handheld probe and form the collimator. The collimator can be optimized for the respective radioactive materials, which may be SPECT tracers, in particular, for different isotopes, and desired sensitivities and resolutions of the detection system. For example, if a relatively high sensitivity is desired, wherein the spatial resolution can be reduced, a shorter collimator can be used.

Figure 3:
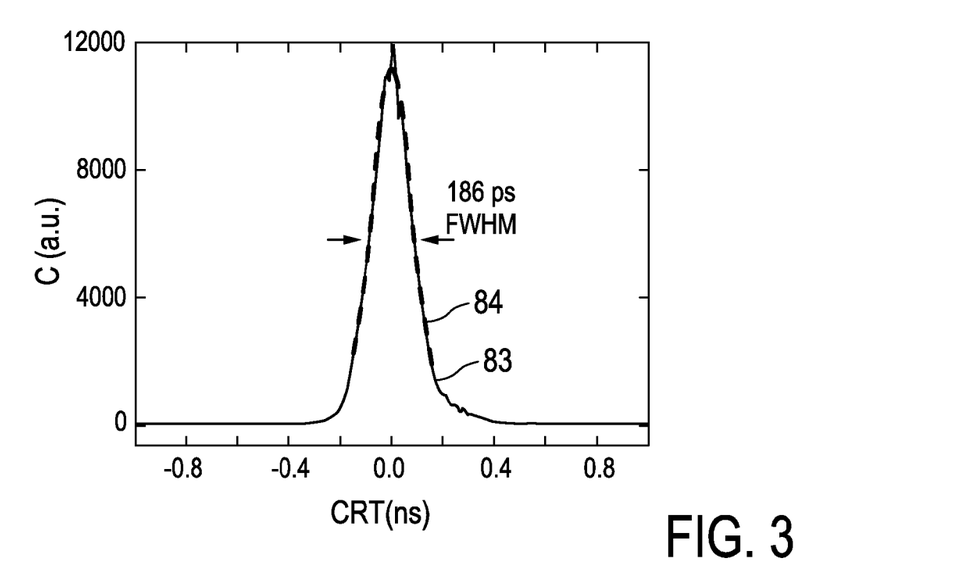
FIG. 3 shows exemplarily the timing resolution of detection elements of the handheld probe.

FIG. 3 shows schematically and exemplarily the counts detected by the array 10 of detection elements in arbitrary units depending on the coincidence resolving time (CRT) in ns. In this example, the full width at half maximum is 186 ps. In other embodiments, the full width at half maximum can also have another value. Preferentially, the full width at half maximum is smaller than 500 ps, further preferred smaller than 250 ps and even further preferred smaller than 150 ps. In FIG. 3, the solid line 83 represents measured counts and the broken line 84 indicates a Gaussian function fitted to the measured counts 83.

If the array of detection elements is based on direct conversion, the corresponding direct conversion materials can be featured as flexible detectors employing standard photolithography and thin film technologies as described in US 2004/0016886 and U.S. Pat. No. 6,856,760, which are herewith incorporated by reference. The direct conversion material is preferentially directly bonded to a read-out ASIC which provides an energy estimate, an arrival time and position information in a digital format. The mechanical arrangement within the handheld probe 5 can be minimized by flexible substrates like polyimide, in particular, Kapton, Upilex, polyester or polyetherimide.

The generated detection signal is provided to the direction determination unit 12 via a data transmission unit 60 and the cable 7 for determining a direction of maximal radioactivity based on the detection signal, which, because it is known which detection element has detected which event, is a spatial detection signal. The direction determination unit 12 differentiates the spatial detection signal and determines the direction of maximal radioactivity based on the differentiated spatial detection signal. The detected direction of maximal radioactivity is then shown on a display 35. For example, an arrow 30 can be shown on the display 35, wherein the arrow 30 is aligned with the detected direction of maximal radioactivity. The handheld probe 5 preferentially comprises a handle 31, wherein the display 35 is preferentially attached to the handle 31. In addition or alternatively, the detected direction of maximal radioactivity can also be shown on a display 17 connected to the control device 19. The determined direction of maximal radioactivity can be shown in realtime on the respective display, in order to allow a user to move the handheld probe 5 within a few seconds to the desired location comprising the radioactive material. The determined direction of maximal radioactivity is preferentially a three-dimensional vector.

The detector elements are preferentially individually readable to allow for differential measurements of the intensity of the detected radiation. The intensity, i.e. the count rate, is determined depending on the axial position along the handheld probe 5 and depending on the radial position with respect to a rotation around the length axis of the handheld probe 5. Since the geometries, in particular, the positions, of the elements of the first and second scintillator arrays 81, 82 are known with respect to the handheld probe 5, a three-dimensional spatial gradient of the count rates can be determined as a direction of maximal radioactivity. For example, if the first scintillator array 81 measures a count rate being larger than the count rate measured by the second scintillator array 82, a spatial gradient of the count rates can be determined, which is aligned substantially parallel to the length axis of the handheld probe 5 and which points to the tip 23 of the handheld probe 5.

The array 10 of detection elements is further adapted to allow detecting an energy resolved spectrum of the detected radiation, wherein the energy application apparatus 1 further comprises an activity determination 13 for determining an activity of the radioactive material depending on the detected energy resolved spectrum. In particular, the detected spectrum can be compared with a target spectrum and the activity of the radioactive material can be determined depending on the comparison. The activity can be shown, for example, in Bq/ml. The feedback with the activity 33, which is preferentially shown on the display 35 and/or the display 17, gives an operator the confidence that the desired location, i.e. the desired hotspot, has been found.

Figure 4:
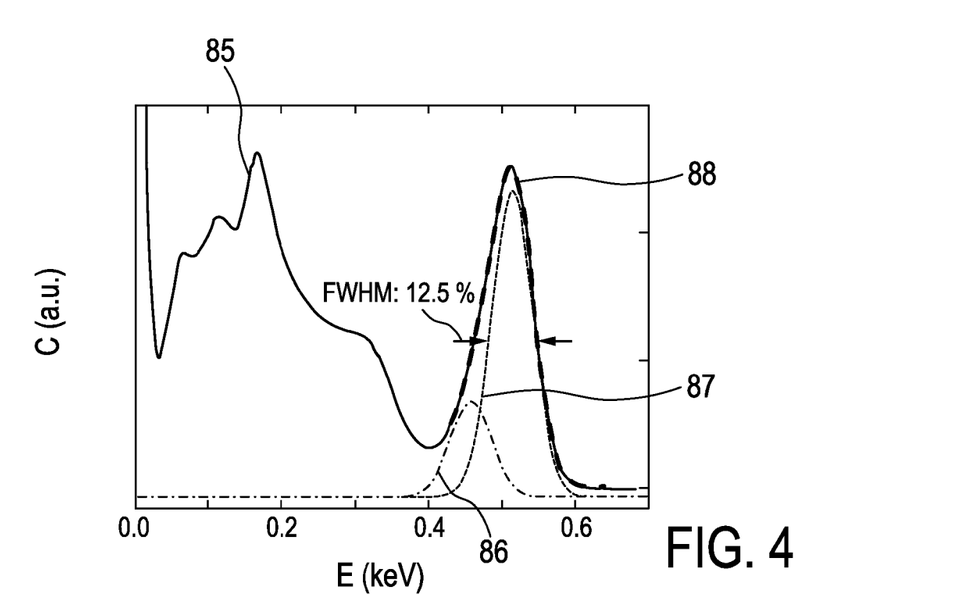
FIG. 4 shows exemplarily the energy spectrum of radiation detected by the detection elements.

FIG. 4 shows schematically and exemplarily a spectrum 85 depending on the energy E in keV. The dashed curve 87 indicates a target spectrum and the dashed-dotted curve 86 indicates an escape peak. A combination of these two curves 86 and 87 is fitted to the spectrum 85, resulting in a fitted curve 88. The peak of the fitted curve 88 is indicative of the activity of the radioactive material with the target spectrum 87. Assignments between the peak of the fitted curve 88 and the activity can be determined by calibration measurements, wherein the peak of the fitted curve 88 is determined, while the activity of the radioactive material is known. In other embodiments, the escape peak may not be considered. Moreover, also the peak of the original spectrum 85 within an energy range, which is defined by the respective radioactive material, can be used for determining the activity.

The energy spectrum is useful for several reasons. For example, the energy spectrum can be used to detect the correct energy peak of the radioactive material, i.e. of the radioactive tracer, in use. Other tracers, for example, from previous investigations or treatments, can therefore be rejected. For instance, I-123 emits at 159 keV and can be distinguished from FDG emitting at 511 keV. Moreover, only the unscattered events, i.e. events, which are not affected by scattering within the person and which are mainly in the energy peak of the spectrum, can be used to find the correct three-dimensional gradient and the absolute values of intensity. The scattered events have lower energies and can therefore be discarded by using energy windowing. In particular, depending on the desired radioactive material a corresponding energy window can be automatically provided, wherein for determining the three-dimensional gradient and preferentially also the activity, only events having energies within the respective energy window are used. In addition, absolute quantification, for example, the absolute determination of the activity, can be performed by not only using the peak values, but by also using the further events located within the respective energy window. The detection elements are preferentially adapted to provide temporal information for each detected event. In particular, each event comprises a time stamp. The time stamp can be used for clustering detected events, in particular, detected gamma ray events, which are detected in neighboring detector elements and which have substantially the same time stamp. This can lead to a reduced detector scatter.

The x-ray unit 9 is preferentially a miniature x-ray tube operating at a modest voltage of, for example, 50 kV. The x-ray tube can be turned off and on, wherein the radiation energy is relatively low and thus has a short range. The mean energy is, for example, within a range of 20 to 30 keV. This implies that a treatment does not have to be carried out in a standard radiotherapy bunker as it would be the case, if radioactive material would also be used for treating purposes. Healthy tissue of a person and treatment personal are spared, and cumbersome isotope logistics and regulations can be disregarded. Such an x-ray tube is provided, for example, by the company Xoft, wherein this x-ray tube has a diameter of 2.4 mm excluding cooling and operates at 50 kV and 300 µA. It gives a dose rate of approximately 0.6 Gy at 3 cm distance in tissue and is thus classified as a high dose rate source.

The dose and emission spectra of the x-ray unit can be controlled by a detection and x-ray application control unit 14. For example, the detection and x-ray application control unit 14 can be adapted to control the high voltage and current of the x-ray unit such that x-rays having a desired dose and emission spectra are emitted by the x-ray unit.

In this embodiment, the radiation is emitted in radial direction 40. The radiation can be emitted radially omnidirectionally, i.e. similarly in each radial direction, or with different intensities in different rotational angular ranges with respect to a rotation around the length axis of the handheld probe. For example, in a certain rotational angular range the intensity of the x-ray radiation can be larger than in the remaining rotational angular range, in particular, only in the certain rotational angular range x-ray radiation may be emitted.

The array 10 of detector elements is switchable between a counting mode, in which single radioactive events are detected, and an integrating mode. The detection and x-ray application unit 14 is preferentially adapted to control the location detection unit 8 such that the array 10 of detection elements is operated in the counting mode, when the x-rays are not applied, and that the array 10 of detection elements is operated in the integrating mode, when the x-rays are applied, wherein, when the x-rays are applied, the array 10 of detection elements detects scattered x-rays scattered by the object and wherein the detection and x-ray application control unit 14 is adapted to control the x-ray unit 9 depending on the scattered x-rays.

The energy application apparatus 1 further comprises a positioning unit 15 for determining the position of at least a portion of the energy application apparatus 1 with respect to a reference coordinate system. In this embodiment, the positioning unit 15 determines the position of the handheld probe 5 with respect to a reference coordinate system. The positioning unit comprises, for example, at least one of a differential GPS sensor, a FBG sensor, an EM sensor, an accelerometer sensor, et cetera.

The energy application apparatus 1 further comprises an image providing unit 16 for providing an image of the object 2, which is registered with respect to the reference coordinate system, wherein the display 17 is adapted to show the determined position of at least a portion of the energy application apparatus 1 with respect to the object 2. In particular, the display 17 shows the complete handheld probe 5 or a tip of the handheld probe 5 with respect to the object 2.

The energy application apparatus is preferentially adapted to be used in an interventional procedure, wherein the provided image was preferentially generated before the interventional procedure. The image providing unit 16 is therefore preferentially a storing unit for storing the image or a receiving unit for receiving the image via a wired or wireless data connection. The image is, for example, a PET image, a SPECT image, a CT image, a MR image et cetera. The position of the handheld probe 5 is preferentially determined in realtime, thereby allowing a user to navigate the handheld probe 5 based on the determined position shown with respect to the object on the display 17.

The reference coordinate system is, for example, a coordinate system defined by the imaging modality which generated the provided image. The positions of the elements shown in the image are therefore known with respect to the reference coordinate system. The positioning unit 15 and the position calculation unit 18 are then preferentially adapted to determine the position of the handheld probe 5 also with respect to the coordinate system defined by the imaging modality, in order to register the determined position of the handheld probe 5 with the provided image.

The position of the handheld probe 5 within the provided image can be used to get close to the target, for example, to a lesion to be treated. The fine navigation is then preferentially performed by using the location detection unit 8.

Figure 5:
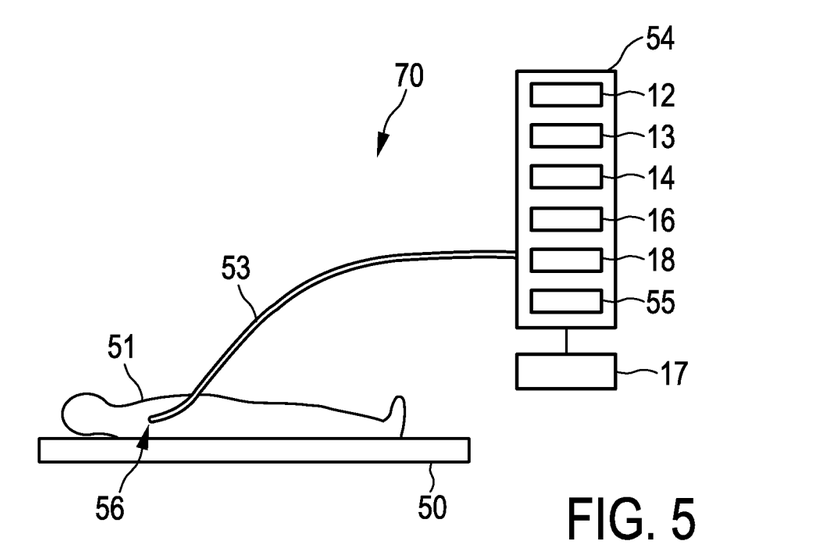
FIG. 5 shows schematically and exemplarily another embodiment of an energy application apparatus for applying energy to an object.

FIG. 5 shows schematically and exemplarily a further embodiment 70 of an energy application apparatus for applying energy to an object. The energy application apparatus 70 shown in FIG. 5 is similar to the energy application apparatus 1 described above with reference to FIG. 2. In particular, also the energy application apparatus 70 shown in FIG. 5 comprises a direction determination unit 12, an activity determination unit 13, a detection and x-ray application control unit 14, an image providing unit 16 and a display 17. The main difference between the energy application apparatus 70 shown in FIG. 5 and the energy application apparatus 1 shown in FIG. 2 is the catheter 53 which is used instead of the handheld probe 5. In FIG. 5, the tip 56 of the catheter 53 has been introduced into a person 51 arranged on a table 50. The control unit 54 comprises a navigation unit 55 for navigating the catheter 53, in particular, the catheter tip 56 to a desired location within the person 51. An embodiment of the catheter tip 56 is exemplarily shown in more detail in FIG. 6.

Figure 6:
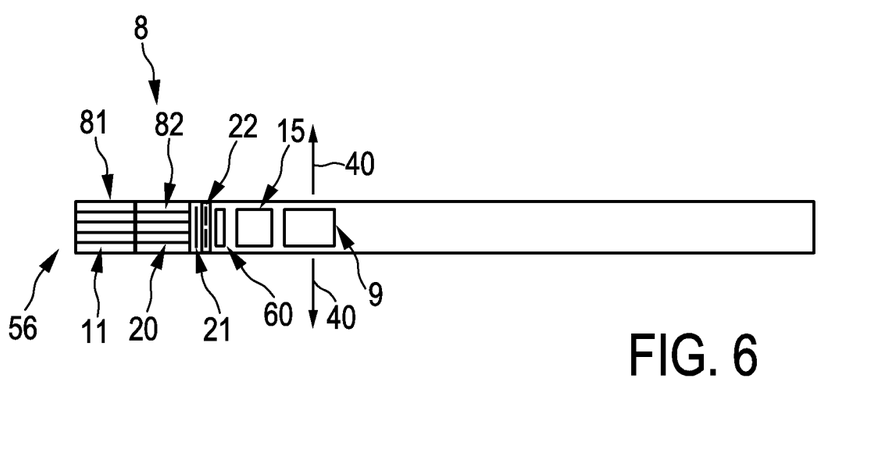
FIG. 6 shows schematically and exemplarily a catheter tip of the energy application apparatus shown in FIG. 5.

The catheter tip 56 is similar to the handheld probe 5 described above with reference to FIG. 2. In particular, also the catheter tip 56 comprises first and second radial scintillator arrays 81, 82 with collimators 11, 20, light guides 21 and digital SiPMs 22, which form an array of detector elements 10 of a location detection unit 8. Moreover, also the catheter tip 56 comprises a positioning unit 15 and an x-ray unit 9. Preferentially, the location detection unit 8 and the x-ray unit 9 have a combined size, which allows these components to be located within a small catheter having a diameter of, for example, 2 to 3 mm.

Figure 7:
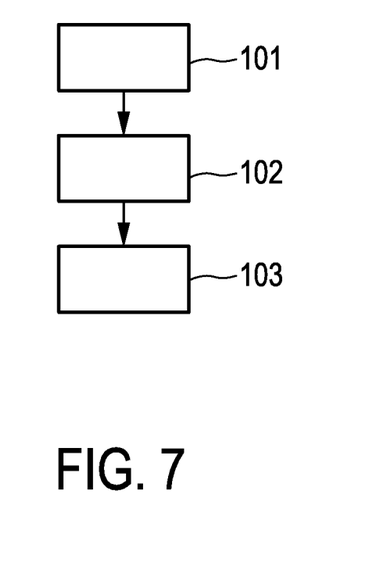
FIG. 7 shows a flowchart exemplarily illustrating an embodiment of an energy application method for applying energy to an object.

In the following an embodiment of an energy application method for applying energy to an object will exemplarily be described with reference to a flowchart shown in FIG. 7.

In step 101, the interventional device, for example, the handheld probe 5 or the catheter tip 56, are navigated to a desired location within a person. This coarse navigation of the interventional device can be performed by using the positioning unit 15 and a registered pre-acquired image of the person, wherein by using the positioning unit 15 the position of the interventional device within the object can be tracked and shown on the display 17. In step 102, a location with radioactive material, which is already present within the person, for example, by injecting a radioactive tracer, is detected, and, if needed, the interventional device can be navigated to the location with the radioactive material such that, in step 103, x-rays can be applied to the detected location by the x-ray unit 9.

In particular, the energy application apparatus can be used by an operator who is, for example, a physician, for minimal invasive procedures, wherein the patient has already received a radioactive tracer, i.e. the radioactive material. Optionally, a reference data set representing a functional image can be used for realtime tracking of the interventional device on the display. Instead of a functional image also another image like a morphological image can be used for realtime tracking. If the functional image is used as a reference data set, image data could be taken from the same injection procedure. For three-dimensional realtime guidance with the reference data set the three-dimensional positioning system, i.e. the positioning unit 15, on or within the interventional device can be initialized with a few reference points before starting the guidance. The reference points are, for example, the nose, the chest, the hips, et cetera.

For example, reference points can be identified in the reference data set using known corresponding detection techniques. The interventional device can then be arranged at these reference points, and the position of the reference points can be measured with the three-dimensional positioning system. Finally, the reference points identified in the reference data set and the measured corresponding positions can be used for registering the positioning system with the reference data set. Also other known rigid or non-rigid registration techniques can be used for registering the positioning system with the reference data set, which may be a pre-acquired image or a currently acquired fluoroscopy image.

The activity of the radioactive material and the gradient, i.e. the direction of maximal activity or the direction of the closest hotspot, can be determined as described above and shown to the operator, for example, on an external display connected to the control device and/or, if the interventional device is a handheld probe with a display, on this display on the handheld probe. This information provided to the operator enables the operator to effectively steer the interventional device to the desired location. If a visualization with the reference data set is provided, also the position of neighboring hotspots can be identified to verify that the right spot is selected.

If the right spot has been found, the x-ray unit can be used to apply x-rays to this spot. For example, the radioactive tracer can label a local tumor, which can be treated by using the x-rays.

Although the interventional devices described above with reference to FIGS. 2 and 8 comprise certain components, the interventional devices can also comprise further components. For example, the interventional device can comprise a marking unit like an ink unit for marking a determined location comprising radioactive material.

Although in the above described embodiments the energy application apparatus has been described as being used for applying x-rays to a location, which has been detected as comprising radioactive material, the energy application apparatus can also be used for outcome control. In particular, after x-rays have been applied to a certain location, the interventional device can be used to detect whether still radioactive material having an activity above a predefined threshold is present at the location. If the radioactive material having an activity above a predefined threshold is still present, the x-rays may be applied again for further treating the respective location.

Commonly used are NaI scintillation probe or handheld Geiger counters containing a gas-filled tube which discharges electrically when ionizing radiation passes through it. These detectors are bulky having a width of, for example, more than 10 mm, are not quantitative and not directional. In contrast, the energy application apparatus of the present invention, in particular, the interventional device, can be adapted to be smaller such that it can be used in minimally invasive operations for detecting radioactively enriched units in vivo precisely, because of the directionality, and accurately, because of the quantization.

The energy application apparatus can be adapted to irradiate and treat stenosis and high risk plaque. Moreover, the energy application apparatus can be an integrated catheter-based system for detection and treatment of radioactively enriched lesions. The possible clinical applications include high-accuracy treatment of primary or metastatic cancerous lesions such as lymph nodes or tumors of liver and bowel. The minimal invasive detection and treatment may be carried out without realtime image guidance and can thus save valuable costs and can simplify the workflow.

The energy application apparatus can be adapted to detect and treat active plaques in vessels like the aorta or the carotid artery. PET-CT can generally be used for detecting active plaque which is the plaque with inflammatory tissue response. These are the lesions most prone to rupture and severe attendant phenomena. Instead of treating the active plaque in interventional PET-CT, the energy application apparatus of the present invention can be adapted to detect FDG-enriched plaques, map these plaques to pre-registered PET-CT images and treat the detected plaques using the above described minimally invasive interventional device. The PET-CT image can be an anatomical CT image shown in grey scale overlayed with a colored PET image, which shows, for example, functional data like the FDG uptake indicating glucose consumption.

The energy application apparatus can therefore be adapted to perform a lesion treatment outside of an imaging theater, which can save costly imaging time as well as extra radiation burden, which would be needed, if radioactive material would also be used for treating a lesion.

The control device can be adapted to power and control the interventional device. The control device can be adapted to send down to the interventional device parameters like calibration parameters, configuration parameters et cetera and the data to handle the display, if the interventional device is a handheld probe with a display, and the control device preferentially acquires the actual energy, time and position information of each registered event detected by the location detection unit. If the interventional device also comprises a positioning unit for determining the three-dimensional position of the interventional device, also this determined three-dimensional position or data indicating the three-dimensional position can be transferred to the control device, in order to allow the control device to visualize the determined three-dimensional position of the interventional device within an image of the object to be treated.

The location detection unit, in particular, the array of detector elements, is preferentially adapted to detect gamma radiation. The location detection unit can therefore also be regarded as being a miniaturized gamma probe.

Figure 8:
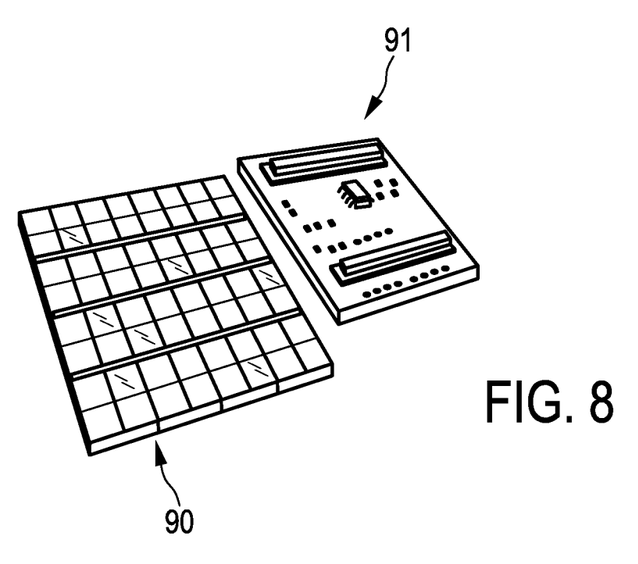
FIG. 8 shows schematically and exemplarily a two-dimensional array of detection elements to detect scintillation light.

Although in the embodiments described above with reference to FIG. 2 and FIG. 6 the array of detection elements is adapted to radially detect the radiation and the x-ray unit is adapted to emit radiation also radially, in other embodiments the interventional device can also provide other detection and emission directions. For example, the interventional device can be adapted to frontally, i.e. parallel to the length axis of the interventional device, detect radiation and emit radiation. Moreover, in an embodiment a substantially planar two-dimensional array of photo detectors can be used as schematically and exemplarily shown in FIG. 8. FIG. 8 shows schematically and exemplarily a front side 90 and a back side 91 of a photo detector with dSiPMs having an 8×8 crystal matrix for forming an array of 8×8 detection elements, wherein each detection element has a detection area with side length of a few mm or less. A scintillation array (not shown in FIG. 8) is mounted on top of the front side 90 of the photo detector.

Although FIG. 2 a cable 7 is shown for connecting the handheld probe 5 with the control device 19, also a wireless communication between the handheld probe 5 and the control device 19 can be used for exchanging data between the handheld probe 5 and the control device 19. If a wireless communication is used, the handheld probe 5 can comprise a local energy source like a local battery, in particular, located in the handle 31, for powering the electrical components of the handheld probe 5.

The energy application apparatus can be adapted to be used in sentinel node procedures and to offer surgeons the possibility to expand current sentinel node techniques to promising new applications like in colon cancer.

Although in the above described embodiments a certain x-ray unit of the company Xoft has been described, the x-ray unit can also be another unit like the x-ray unit for interoperative radiotherapy provided by the company Zeiss, where only the anode part of the x-ray tube is inserted in a still open tumor cavity.

The use of x-rays for treating lesions has the advantage that a well-defined and predictable treated volume can be obtained, in particular, in contrast to using radiofrequency ablation or cryotherapy, in which heat propagation in tissue is strongly dependent on circulation.

Although in the embodiments described above with reference to FIGS. 2 and 8 the interventional device is a handheld probe and a catheter, respectively, the interventional device can also be another device, which comprises at least a location detection unit being usable for detecting the location with radioactive material and an x-ray unit for applying x-rays to the detected location like a needle.

Although in the above described embodiments a certain arrangement of detector elements has been described, the detection elements can also be arranged in another way. For example, two or more regions of detector areas can embrace the x-ray unit. In particular, the above mentioned handheld probe can comprise a cylindrical holder covered on its outside with the detection elements, wherein the x-ray unit can be contained within the detector-covered cylinder. Before the x-rays are applied, the x-ray unit may be displaced by sliding out the detector-covered cylinder to emerge at the distal end of the handheld probe. The detector elements can also be arranged as several chips around the distal tip of the interventional device, wherein the x-ray unit can be placed adjacent to the detection elements.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the calculation of the direction of maximal activity and the calculation of the activity of the radioactive material performed by one or several units or devices can be performed by any other number of units or devices. The calculations and/or the control of the energy application apparatus in accordance with the energy application method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An energy application apparatus for applying energy to a body of a patient, wherein the patient comprises a location with radioactive material and wherein the energy application apparatus comprises: a location detection unit being usable for detecting the location with the radioactive material, an x-ray unit for applying x-rays to the detected location of the patient, and an insertable interventional device configured for being inserted into the body of the patient, including at least a part of the location detection unit and at least a part of the x-ray unit such that the location with the radioactive material is detectable and x-rays are applicable to the detected location via the interventional device, and wherein the location detection unit comprises an array of detection elements for detecting radiation from the radioactive material and for generating a detection signal being indicative of the detected radiation, wherein the array of detection elements is adapted to generate a spatial detection signal depending on the location of the respective detection element, wherein the energy application apparatus comprises a direction determination unit for determining a direction of maximal radioactivity based on the spatial detection signal, and wherein the direction determination unit is adapted to differentiate the spatial detection signal and to determine the direction of maximal radioactivity based on the differentiated spatial detection signal.

2. The energy application apparatus as defined in claim 1, wherein the energy application apparatus comprises an output unit for outputting the detected direction of maximal radioactivity.

3. The energy application apparatus as defined in claim 1, wherein the array of detection elements is adapted to allow detecting an energy resolved spectrum of the detected radiation, wherein the energy application apparatus further comprises an activity determination unit for determining an activity of the radioactive material depending on the detected energy resolved spectrum.

4. The energy application apparatus as defined in claim 1, wherein the array of detection elements is switchable between a counting mount, in which single detected radioactive events are detected, and an integrating mode, wherein the energy application apparatus further comprises a detection and x-ray application control unit for controlling the location detection unit such that the array of detection elements is operated in the counting mode; when the x-rays are not applied, and that the array of detection elements is operated in the integrating mode, when the x-rays are applied, wherein when the x-rays are applied, the array of detection elements detects scattered x-rays scattered by the patient and wherein the detection and x-ray application control unit is adapted to control the x-ray unit depending on the scattered x-rays.

5. The energy application apparatus as defined in claim 1, wherein the energy application apparatus further comprises a positioning unit for determining the position of at least a portion of the energy application apparatus with respect to a reference coordinate system.

6. The energy application apparatus as defined in claim 5, wherein the energy application apparatus further comprises an image providing unit for providing image of the patient, which is registered with respect to the reference coordinate system, and a display for showing the determined position of at least the portion of the energy application apparatus with respect to the patient.

7. A control device for controlling the interventional device as defined in claim 1, wherein the control device is adapted to control at least one of a) the location detection unit for controlling the detection of the location with radioactive material and b) the x-ray unit for controlling the application of x-rays to the detected location.

8. An energy application method for applying energy to an body of a patient with an energy application apparatus, wherein the patient comprises a location with radioactive material and wherein the energy application method comprises: inserting an insertable device into the body of the patient; with an array of radiation detector mounted to the insertable device, detecting radiation from the radioactive material; determining a location of the radioactive material relative to a location of the insertable device based on an output of the array of radiation detectors; and navigating the insertable device towards the radioactivity based on the determined location of the radioactive material relative to the location of the insertable device; repeatedly updating the determined location of the radioactive material relative to the location of the insertable device during navigating; applying x-rays to the detected location of the radioactive material with an x-ray tube mounted to the insertable device when the x-ray tube is adjacent the location of the radioactive material.

9. A non-transitory computer-readable medium carrying program code for causing a computer apparatus to perform the method as defined in claim 8.

10. The method as defined in claim 8, further including: injecting the patient with a radioactive tracer which accumulates in a tumor to define the location with radioactive material, the x-ray tube being controlled to apply x-rays to the tumor.

11. The method as defined in claim 10, wherein the x-ray tube is operated at a sufficiently low power level such that the x-ray tube irradiates the tumor while minimizing radiation of tissue around the tumor.

12. The method as defined in claim 8, further including:
determining a direction from a tip of the insertable device to the tumor; and
displaying an indication of the direction on a display device.

13. The method as defined in claim 12, further including:
manually manipulating the insertable device based on the displayed indication of the direction to bring the x-ray tube adjacent the location of the radioactive material.

14. The method as defined in claim 12, further including: generating a diagnostic image of the patient with a diagnostic imaging device; and displaying the diagnostic image and the indication of the direction on a display device in a common coordinate system.

15. The method as defined in claim 8, further including:
computer controlling the insertable device to navigate to the location of the radioactive material with a computer apparatus; and
with the computer controlled apparatus, actuating the x-ray tube to irradiate the location of the radioactive material while minimizing irradiation of the surrounding locations when the x-ray tube is adjacent the location.

16. An energy application apparatus for applying energy to a target tissue which absorbs a radio-active tracer, the target tissue being interior to a subject, the energy application apparatus comprising:
an insertable device having a tip configured to be inserted into the subject;
an x-ray generator mounted to the insertable device adjacent the tip, the x-ray generating being configured to be selectively energized to apply x-rays to tissue interior to the subject adjacent the insertable device;
an array of radiation detection elements to be mounted to the insertable device adjacent the tip, the radiation detection elements being configured to detect radiation emitted by the radioactive tracer;
a control computer apparatus programmed to determine a direction of maximal radioactivity from signals from the array of radiation detection elements; and
a display device configured to display an indication of the direction determined by the computer apparatus.

17. The energy application apparatus as defined in claim 16, wherein the control computer apparatus is further configured to determine when the x-ray generator is adjacent the target tissue and further including:
an x-ray generator controller configured to active activate the x-ray generator to emit x-rays when the x-ray generator is adjacent the target tissue that absorbed the radioactive tracer.

18. The energy application apparatus as defined in claim 17, wherein the detector array is configured to operate in a counting mode when the x-ray generator is not activated to emit x-rays and in an integrating mode when the x-ray generator is activated to generate x-rays.

19. The energy application apparatus as defined in claim 16, further including:
an imaging apparatus configured to generate a diagnostic image of a region of the subject including the target tissue;
wherein the control computer apparatus is further configured to determine a position of the insertable device and the target tissue in a common coordinate system with the diagnostic image; and
wherein the display device is configured to display the diagnostic image and the positions of the target tissue and the insertable device in the common coordinate system.

20. The energy application apparatus as defined in claim 16, wherein the control computer apparatus is configured to control a position of the insertable device based on the signals from the detector array and to control energizing the x-ray generator.

21. The energy application apparatus as defined in claim 16, wherein the insertable device includes a handle such that the insertable device is a handheld device.

* * * * *